US00PP20647P3

(12) United States Plant Patent

Dai et al.

(10) Patent No.: US PP20,647 P3

(45) Date of Patent: Jan. 19, 2010

(54) STRAWBERRY PLANT NAMED 'TAMIR'

(50) Latin Name: *Fragaria ananassa*
Varietal Denomination: TAMIR

(75) Inventors: Nir Dai, Kfar Maas (IL); Zecharia Tanami, Hasmonaim (IL); Sara Slotzky, Or Yehuda (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 17 days.

(21) Appl. No.: 12/080,973

(22) Filed: Apr. 8, 2008

(65) Prior Publication Data

US 2008/0256672 P1 Oct. 16, 2008

(30) Foreign Application Priority Data

Apr. 10, 2007 (IL) ..... 4029/07

(51) Int. Cl.
*A01H 5/00* (2006.01)

(52) U.S. Cl. ..... Plt./209

(58) Field of Classification Search ..... Plt./208, Plt./209
See application file for complete search history.

(56) References Cited

OTHER PUBLICATIONS

Kunihisa, et al., "Development of Cleavage Amplified Polymorphic Sequence (CAPS) Markers for Identification of Strawberry Cultivars," *Euphytica,* 2003, vol. 134, No. 2, pp. 209-215.

*Primary Examiner*—Susan B McCormick Ewoldt
(74) *Attorney, Agent, or Firm*—Foley & Lardner LLP

(57) ABSTRACT

This invention relates to a new and distinct variety of strawberry plant named 'TAMIR'. This new strawberry plant named 'TAMIR' is primarily adapted to the climate and growing conditions of the growing conditions of the Sharon coastal plain, at 32° latitude, located in Israel, and is primarily characterized by low amounts of runners (stolons) production in the propagating nursery; no chilling requirement for flower induction; very early fruit production from the first week of November in Israel; moderate plant size with open, flattened habit; fruiting trusses position level with foliage; large fruit size, orange-red in color; high fruit firmness even in high temperatures; juicy fruit texture with strong flavor; very nice appearance with yellowish achenes over bright red fruit skin; and high field tolerance to powdery mildew.

7 Drawing Sheets

Latin name of the genus and species of the plant claimed: *Fragaria ananassa.*

Variety denomination: 'TAMIR'.

BACKGROUND OF THE INVENTION

The present invention relates to a new and distinct strawberry variety named 'TAMIR'. The variety is botanically known as *Fragaria ananassa* Duch.

The new strawberry 'TAMIR' is a product of a planned breeding program conducted by the inventors, Nir Dai, Zecharia Tanami and Sara Slotzky in Bet-Dagan, Israel. The objective of the breeding program is to develop a new infra short-day strawberry variety having premium fruit quality (appearance, firmness and flavor), which produces high marketable yields from the beginning of November.

This new strawberry 'TAMIR' is a result of a controlled cross made by the inventors in 2000, in Bet-Dagan, Israel. The female or seed parent is strawberry variety designated 'HADAS', registered for PBR in Israel (No. 1860, Date: Jan. 20, 1999) and in Europe (No. EU 6445, Date: Jul. 3, 2000). The male or pollen parent is strawberry variety designated 'HERUT', registered for PBR in Israel (No. 2243, Date: May 2, 2002) and in Europe (No. EU 21583, Date: Dec. 17, 2007). The new strawberry 'TAMIR' was discovered and selected by the inventors as a single flowering plant within the progeny of the stated cross in March of 2001, in controlled environment of an experimental greenhouse in Bet-Dagan, Israel. After its selection, the new variety was asexually propagated by stolons in a nursery located in Bet-Dagan, Israel. The new variety was extensively tested over the following years in few small commercial fields in Moshav Tsofit, Kadima and Qalansawa, Israel. This propagation has demonstrated that the combination of characteristics as herein disclosed for the new cultivar are firmly fixed and retained through successive generations of asexual reproduction. The new cultivar reproduces true to type.

BRIEF SUMMARY OF THE INVENTION

'TAMIR' is primarily adapted to the climate and growing conditions of the Sharon coastal plain, at 32° latitude, located in Israel and to similar climatic regions. This region provides the needed growing conditions of autumn with high temperatures that promote primary plant growth and earliness of fruit production; and mild winter with moderate temperatures and many sunny days with low humidity, maintaining plant vigorous and fruit quality during the production months.

The following traits have been repeatedly observed and are determined to be unique characteristics of 'TAMIR', which in combination distinguish this strawberry plant as a new and distinct variety:

1. Low amounts of runners (stolons) production in the propagating nursery;
2. No chilling requirement for flower induction;
3. Very early fruit production from the first week of November in Israel;
4. Moderate plant size with open, flattened habit;

5. Fruiting trusses position level with foliage;
6. Large fruit size, orange-red in color;
7. High fruit firmness even in high temperatures;
8. Juicy fruit texture with strong flavor;
9. Very nice appearance with yellowish achenes over bright red fruit skin; and
10. High field tolerance to powdery mildew.

Plants of the new strawberry variety 'TAMIR' differ from plants of the parents, 'HADAS', registered for PBR in Israel (No. 1860, Date: Jan. 20, 1999) and in Europe (No. EU 6445, Date: Jul. 3, 2000), and 'HERUT', registered for PBR in Israel (No. 2243, Date: May 2, 2002) and in Europe (No. EU 21583, Date: Dec. 17, 2007) in the characteristics described in Table 1.

TABLE 1

| Characteristic | 'TAMIR' | 'HADAS' Registered | 'HERUT' Registered |
|---|---|---|---|
| Average fruit weight (gm) | 22 gram | 25 gram | 20 gram |
| Unevenness of fruit surface | Absent or very weak | Weak | Weak |
| Insertion of achenes | Level with surface | Level with surface | Slightly below surface |
| Attitude of calyx | Clasping or detached | Clasping or detached | Clasping or detached |
| Firmness of the fruit | Firm | Medium | Medium |
| Plant size | Medium | Medium | Large |
| Average number of stolons | Few | Many | Very many |
| Foliage color (upper surface) | Medium to dark | Dark | Medium to dark |
| Interveinal leaf blistering | Weak | Weak | Weak |
| Vigor | Medium | Medium | Strong |
| Position relative to foliage | Level with | Above | Beneath |

Of the many commercial cultivars known to the present inventor, the most similar in comparison to the new strawberry variety 'TAMIR' is the male or pollen parental cultivar, strawberry variety 'HERUT' (registered for PBR in Israel and Europe). Plants of the new strawberry variety 'TAMIR' differ from plants of strawberry variety 'HERUT' in the characteristics described in Table 2.

TABLE 2

| Characteristic | 'TAMIR' | 'HERUT' Registered |
|---|---|---|
| Average fruit weight (gm) | 22 gram | 20 gram |
| Insertion of achenes | Level with surface | Slightly below surface |
| Attitude of calyx | Clasping or detached | Clasping or detached |
| Firmness of the fruit | Firm | Medium |
| Plant size | Medium | Large |
| Average number of stolons | Few | Very many |
| Fruit color | Orange-red | Red to dark red |
| Fruit tip color | Without green tip | Dominant green tip |
| Foliage size | Medium | Large |
| Inflorescence position relative to foliage | Level with | Beneath |

For its identification, a series of molecular markers have been developed for this new variety. The genetic polymorphic pattern of two Cleavage Amplified Polymorphic Sequence (CAPS) markers (A. APX- MluI and B. CTI-HinfI (Kunihisa et al., 2003)) that differ between the new strawberry cultivar 'TAMIR' and the main commercial Israeli strawberry cultivars, as well as, other widely known strawberry cultivars is shown in FIG. 7.

BRIEF DESCRIPTIONS OF THE PHOTOGRAPHS

The accompanying color photographs illustrate the overall appearance of typical specimens of the new strawberry variety 'TAMIR', at various stages of development as true as it is reasonably possible with color reproductions of this type. Color in the photographs may differ slightly from the color value cited in the botanical description which accurately describes the color of 'TAMIR'. The depicted plant and plant parts of the new strawberry variety 'TAMIR' were taken in Moshav Tsofit, Israel, and are approximately 5 month old.

Figure 1:
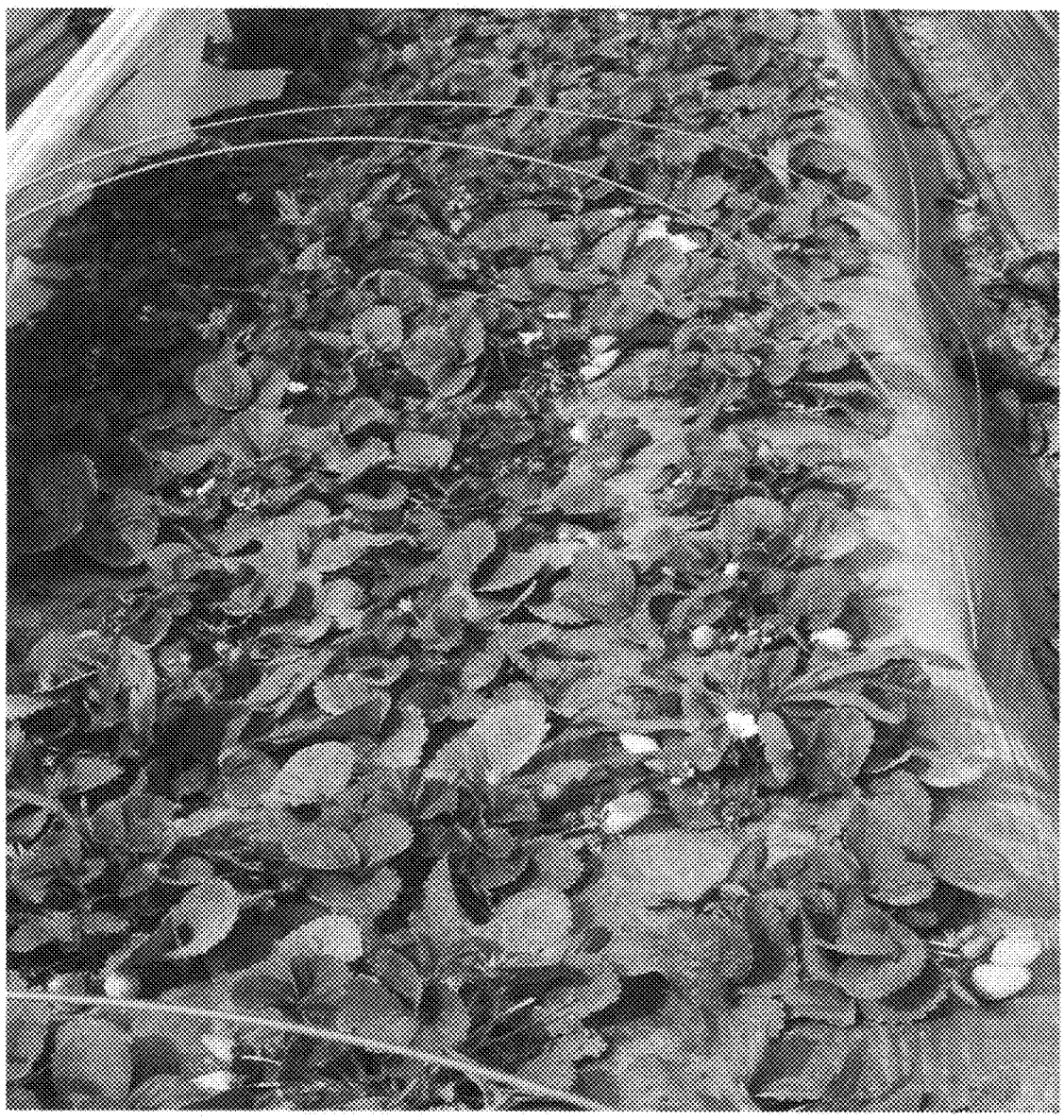
FIG. 1 shows typical fruiting field characteristics of 'TAMIR' taken in February of 2007.
Figure 2:
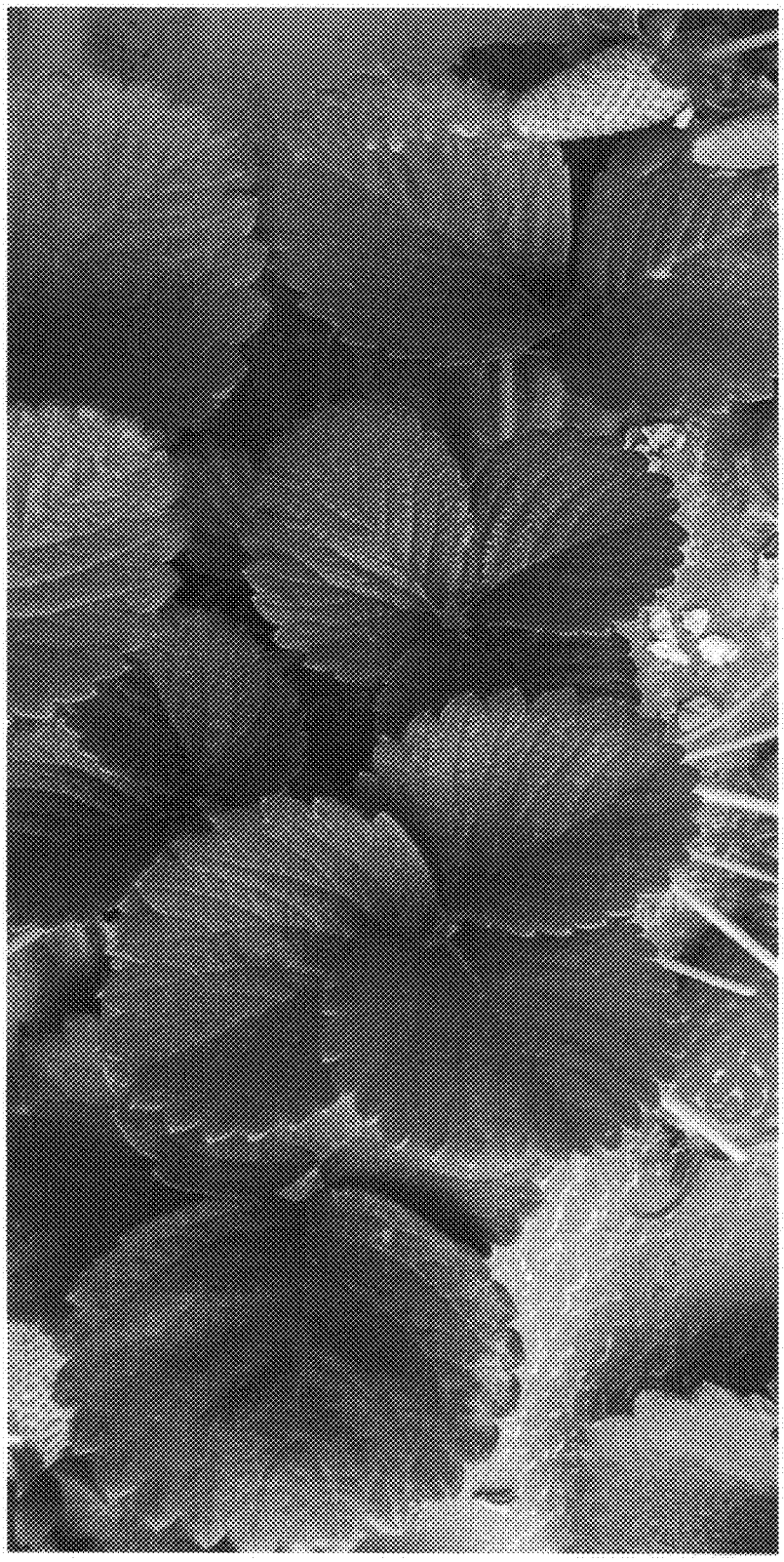
FIG. 2 shows a close-up view of the typical leaf structure of 'TAMIR' taken in February of 2008.
Figure 3A:
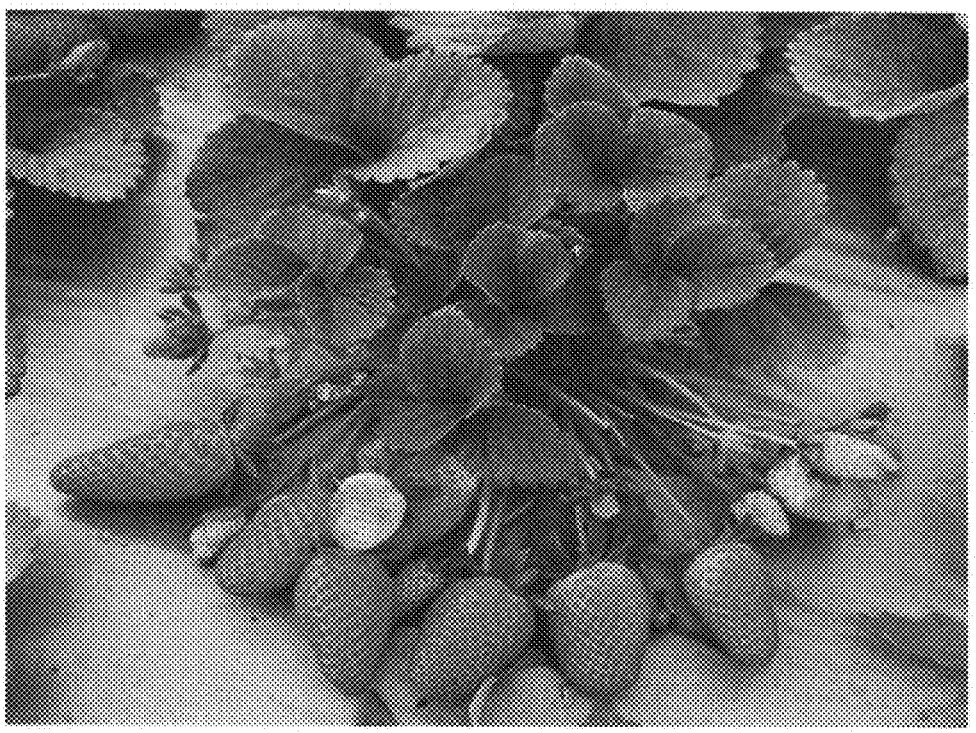
FIG. 3A shows typical mature and immature field fruit of 'TAMIR' taken in February of 2007 and FIG. 3B shows typical mature and immature field fruit of 'TAMIR' taken in February of 2008.
Figure 3B:
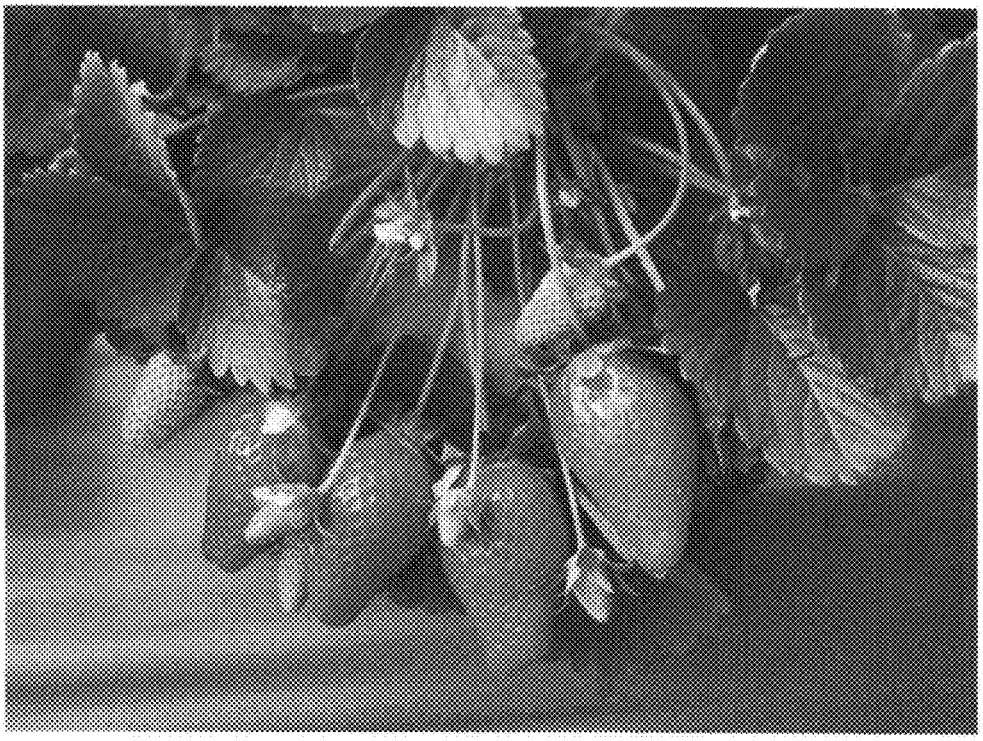
Figure 4:
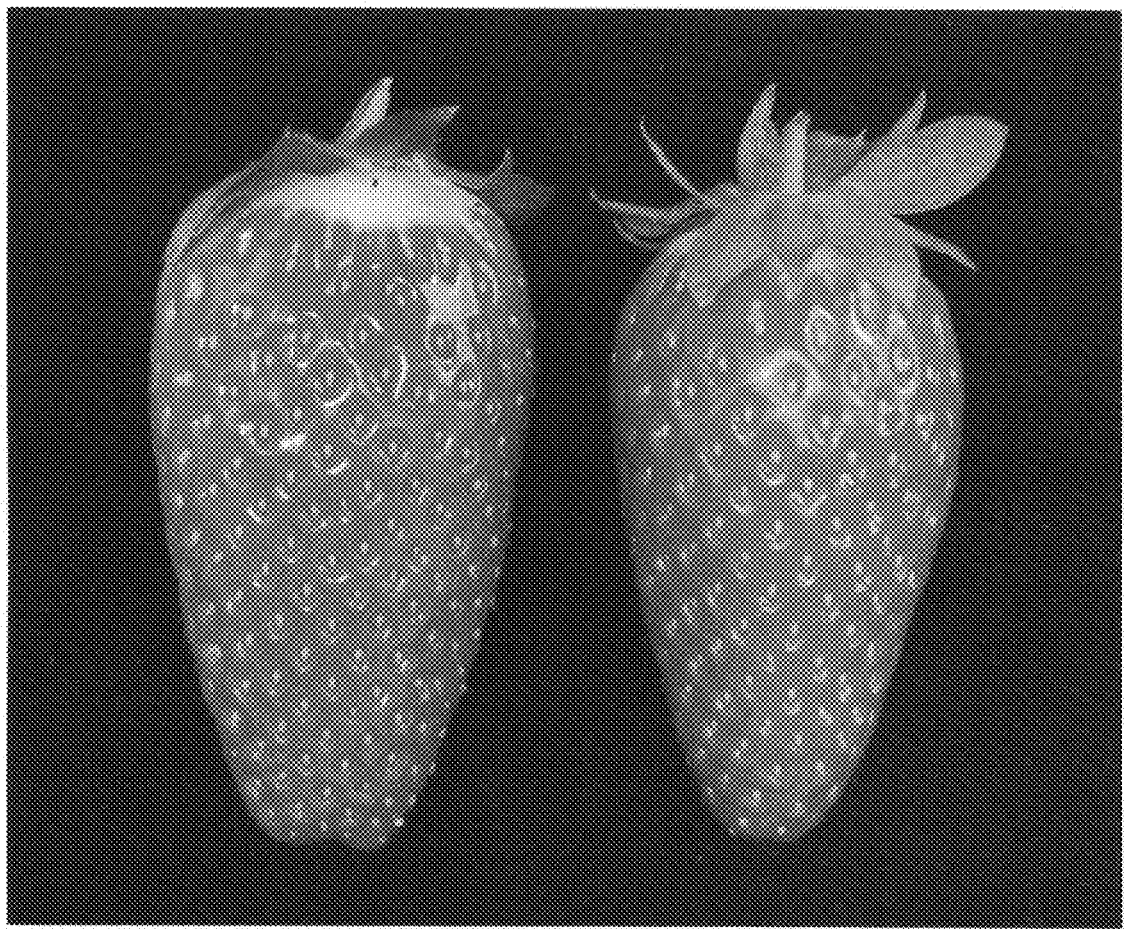
FIG. 4 shows a close-up external view of mature fruit of 'TAMIR' taken in February of 2007.
Figure 5:
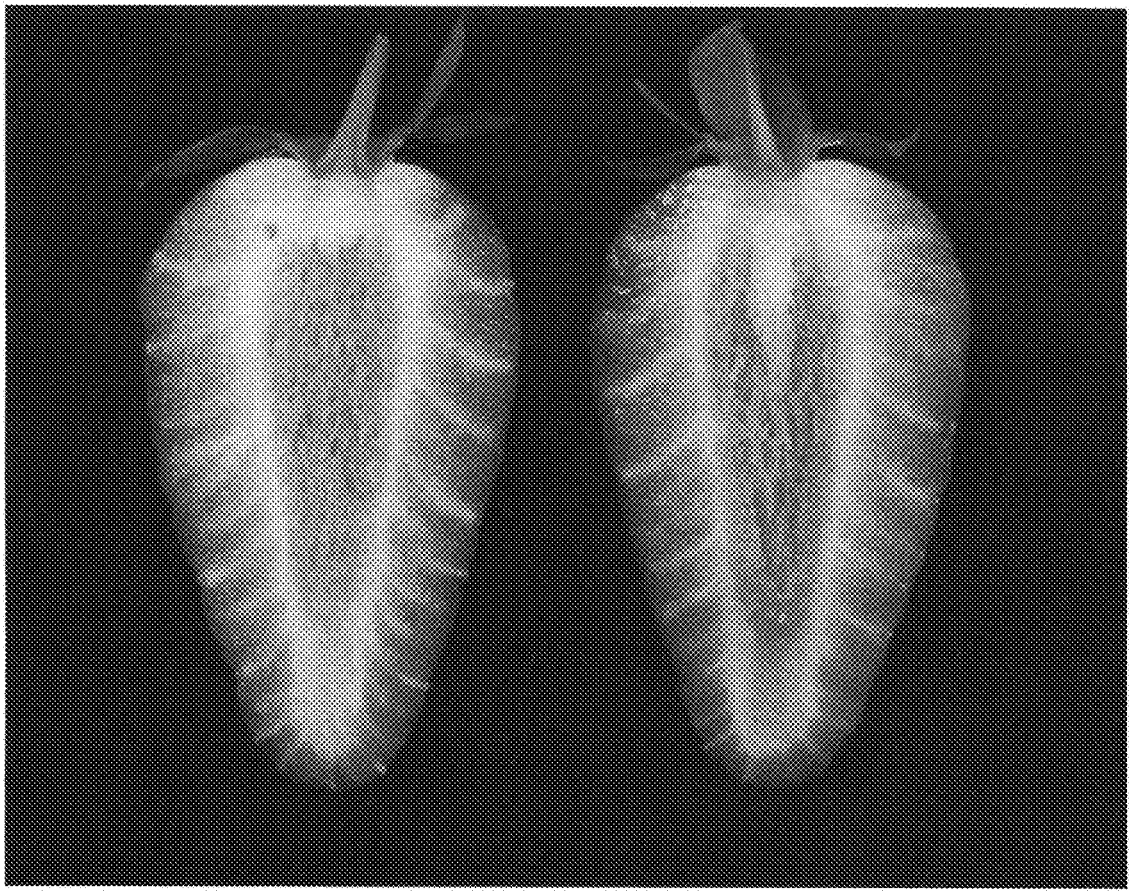
FIG. 5 shows a close-up internal view of mature fruit characteristics of 'TAMIR' taken in February of 2008.
Figure 6:
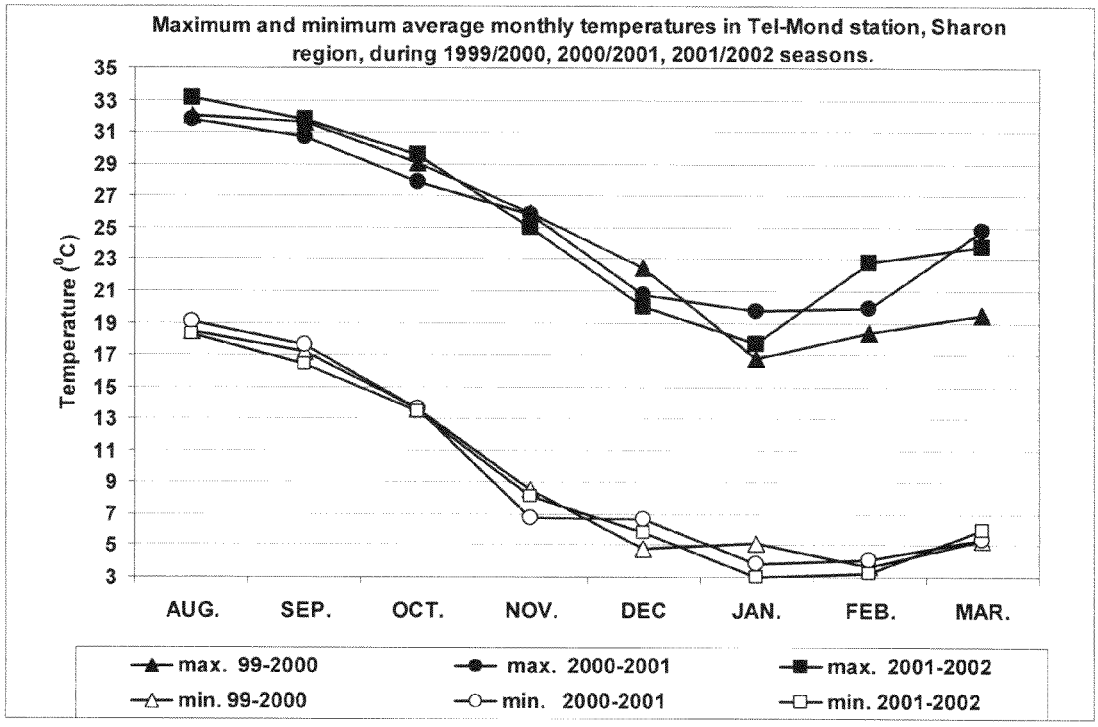

FIG. 6. Average August to March maximum and minimum temperatures, during the main strawberry growing season at the fruit production field.

Figure 7:
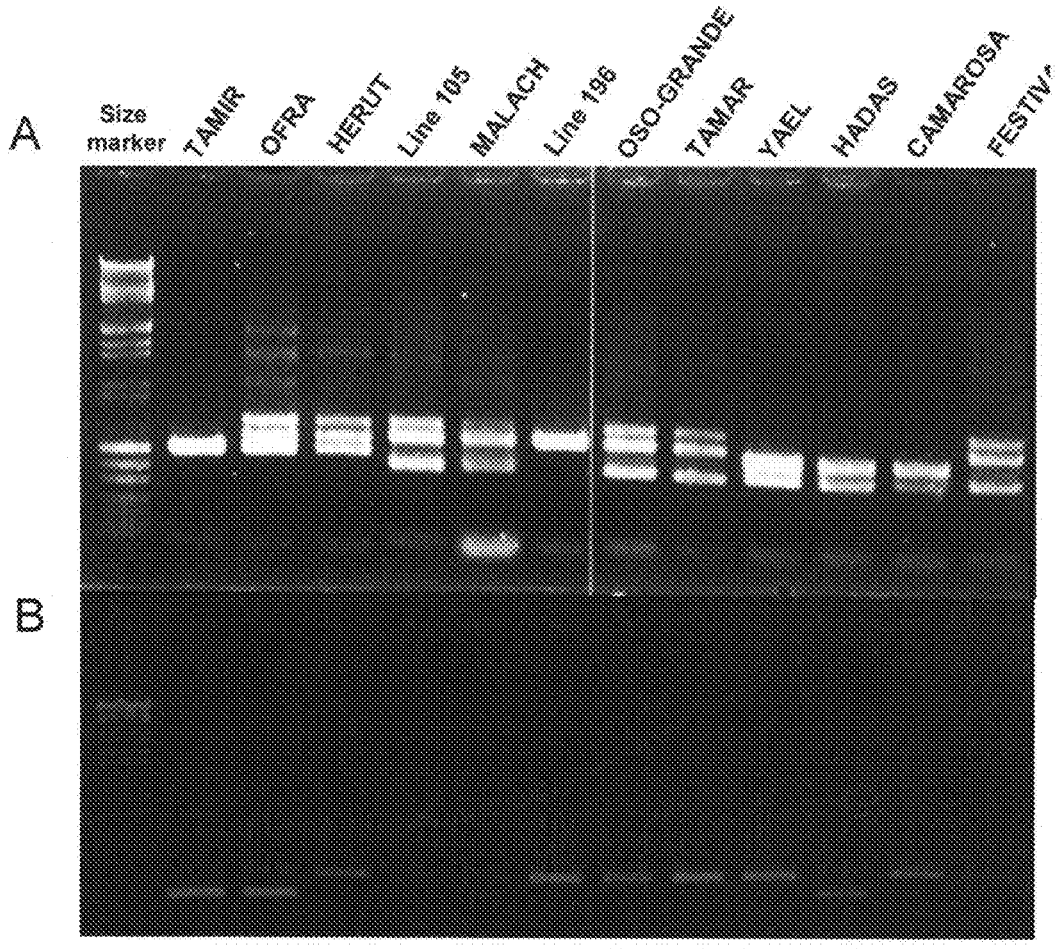

FIG. 7. The genetic polymorphic pattern of 12 strawberry accessions at two CAPS markers: A. APX- MluI and B. CTI-HinfI (following Kunisha, et al. (2003)).

DETAILED BOTANICAL DESCRIPTION

'TAMIR' has not been observed under all possible environmental conditions. The characteristics of the new variety may vary in detail, depending upon variations in environmental factors, including weather (temperature, humidity and light intensity), day length, soil type and location.

The aforementioned photographs, together with the following observations, measurements and values describe the new strawberry variety 'TAMIR', unless otherwise noted, taken during the winter of the growing season 2007–2008 in Moshav Geolim and Bet-Dagan, Israel. The observations, measurements and values were taken from plants of 'TAMIR' dug from a low-elevation nursery located in Moshav Geolim and Bet-Dagan, Israel, during September, 2007 and planted directly, without any chilling, in the same day in the commercial field in Moshav Geolim and experimental greenhouse Bet-Dagan, Israel. Plants of the new strawberry variety 'TAMIR' were grown under conditions which closely approximate those generally used in commercial practice.

Growing conditions at the nursery:

Mother plants provided from an authorized nursery are planted in the beginning of May, in the field nursery at 2.5 m×2.5 m distance. Combination of overhead and drip irrigation with addition of fertilizers is used. The average day/night temperatures during the establishment of the daughter plants, between June to August, are 32° C./18° C. respectively. Runners appear from June, which produce young daughter plants up till mid September, these are then collected and planted directly in the commercial fields.

Growing conditions at the fruit production field:

The bare rooted plants are washed from soil and dipped in Octav (Prochloraz manganese) 2 g/Liter solution to avoid anthracnose. These bare rooted plants are then planted in raised beds with overhead irrigation in 4 rows at 30 cm apart. Distance between plants within rows is 32 cm. During the first month, no fertilizers are added, due to the addition of 60–100 $m^3$/hectar compost during field preparation. About 4 weeks after planting the beds are covered with silvery-black, 30 micron polyethylene. The young plants are pulled out through the pre-prepared holes. From this point on, the plants are irrigated with a drip system with a supply of additional fertilizers, as is typically used in agricultural practice. By the end of October the beds are covered with transparent, 80 micron thick polyethylene tunnels. The average day (max) and night (minimum) temperatures during the cultivation season are shown in FIG. 6.

During winter in Israel, most days have full sunlight and only average of 82 rainy days from August to June, producing about 620 mm precipitation. The commercial fields are not treated with growth regulators and regularly are irrigated and fertilized according to need during fruit production.

Yield observations and fruit quality characteristics are averaged from 2 years of data collected from the 2006 to 2007 and 2007 to 2008 growing seasons. Flower measurements and characteristics are from secondary flowers unless otherwise noted. Fruit characteristics and measurements are from secondary fruit unless otherwise noted.

Color references are made to The Royal Horticultural Society Colour Chart (R.H.S.), except where general colors of ordinary significance are used. Color values were taken under daylight conditions between 10:00 a.m. to noon in Bet-Dagan, Israel. The approximate age of the observed plants is 4 to 6 months.

The following Tables 3 to 9 describe fruit, plant, stolon, foliage, fruiting truss, flower and pest/disease characteristics of the new strawberry 'TAMIR'.

TABLE 3

FRUIT CHARACTERISTICS

| Characteristic | 'TAMIR' |
|---|---|
| Color of mature fruit | Orange-red, RHS 34A |
| Color of internal flesh | Orange-red, RHS 33B |
| Length (cm) | 5 cm to 7 cm |
| Width (cm) | 3.2 cm to 4 cm |
| Ratio length/width | Longer than broad |
| Calyx diameter (cm) | 3.0 cm to 3.5 cm |
| Average weight (gm) | About 22 gram |
| Achene color | Yellow-green, RHS 154B |
| Number of achenes per berry | About 200 |
| Achene weight (mg) | Not relevant |
| Marketable yield (gm/plt) | Monthly yield |
| | Nov. 53 gram/plant |
| | Dec. 143 gram/plant |
| | Jan. 155 gram/plant |
| | Feb. 184 gram/plant |
| | Mar. 232 gram/plant |
| | Apr. 165 gram/plant |
| | May 119 gram/plant |
| | Total: 1051 gram/plant |
| Size | Large |
| Predominant shape | Conical |
| Difference in shapes between primary and secondary fruit | Slight |
| Band without achenes | Narrow |

TABLE 3-continued

FRUIT CHARACTERISTICS

| Characteristic | 'TAMIR' |
|---|---|
| Unevenness of surface | Weak |
| Evenness of color | Slightly uneven |
| Glossiness | Medium to strong |
| Insertion of achenes | Level with |
| Insertion of calyx | Level |
| Attitude of the calyx | Clasping or detached |
| Size of calyx in relation to fruit diameter | Same size |
| Adherence of calyx | Strong |
| Firmness of skin | Not relevant |
| Firmness of flesh | Firm |
| Distribution of red color of the flesh | When viewed in longitudinal section - marginal distribution of orange-red color of flesh of fruit (orange-red color (RHS 33B) towards outer rim of flesh of fruit, and white (RHS N155B) near inner part of flesh of fruit) |
| Hollow center expression | Weak |
| Flavor | Strong |
| Soluble solids (% brix) | 8.5-10% |
| Time of first flowering | Very early, from the beginning of October |
| Time of first harvesting | Very early, from the beginning of November |
| Harvest period | November to June |
| Type of bearing | Partially remontant |

TABLE 4

PLANT CHARACTERISTICS

| Characteristic | 'TAMIR' |
|---|---|
| Height (cm) | 8 cm to 13 cm |
| Spread (cm) | 28 cm to 33 cm |
| Size | Medium |
| Habit | Flattened - globular |
| Density | Sparse. |
| Vigor | Moderate |

TABLE 5

STOLON CHARACTERISTICS

| Characteristic | 'TAMIR' |
|---|---|
| Average number per plant | Few |
| Fruiting field | Few, until the first harvest |
| Average Length: | About 2.5 m |
| Color: | Green, RHS 144B |
| Anthocyanin coloration | Greyed-red RHS 181C |
| Anthocyanin intensity | Very weak to weak |
| Diameter at bract (mm) | 3 mm to 4 mm |
| Pubescence | Strong |

TABLE 6

FOLIAGE CHARACTERISTICS

| Characteristic | 'TAMIR' |
|---|---|
| Foliage: | |
| Color of upper surface | Medium to dark green, RHS 137A |
| Color of under side | Light green, RHS 138B |
| Shape in cross section | Slightly concave |
| Interveinal blistering | Weak |

TABLE 6-continued

| FOLIAGE CHARACTERISTICS | |
|---|---|
| Characteristic | 'TAMIR' |
| Glossiness | Weak to medium |
| Number of leaflets | Only three |
| Terminal Leaflet: | |
| Length (cm) | 6 cm to 8 cm |
| Width (cm) | About 6 cm |
| Length/width ratio | Slightly longer than broad |
| Incision of margin | Crenate |
| Shape of base | Rounded |
| Shape of teeth | Rounded |
| Petiole: | |
| Length (cm) | 8 cm to 9 cm |
| Diameter (mm) | About 3 mm |
| Petiolule length (mm) | 4 mm to 7 mm |
| Pubescence | Dense |
| Attitude of hairs | Outwards |
| Stipule: | |
| Length (mm) | About 30 mm |
| Width (mm) | About 10 mm |
| Anthocyanin coloration | None |
| Color | Yellow-green, RHS 145B |

TABLE 7

| FRUITING TRUSS CHARACTERISTICS | |
|---|---|
| Characteristic | 'TAMIR' |
| Length (cm) | About 6 cm |
| Position relative to foliage | Level with |
| Pubescence | Strong |
| Anthocyanin intensity | None |
| Attitude at first pick | Prostrate |
| Difference between primary and secondary flower | Very slight |

TABLE 8

| FLOWER CHARACTERISTICS | |
|---|---|
| Characteristic | 'TAMIR' |
| Petal color | |
| Mature (upper) | White, RHS 155B |
| Mature (lower) | White, RHS 155B |
| Immature (upper) | Not relevant |
| Immature (lower) | Not relevant |
| Petal shape | |
| Overall | Rounded |
| Apex | Rounded |
| Base | Rounded |
| Petal length (mm) | 10 mm to 12 mm |
| Petal width (mm) | 11 mm to 13 mm |
| Petal length/width ratio | Slightly broader than long |
| Number of petals/flower | Typically 5, sometimes 6 |
| Sepals color | |
| Mature (upper) | Medium green, RHS 137C |
| Mature (lower) | Light green, RHS 138B |
| Immature (upper) | Not relevant |
| Immature (lower) | Not relevant |
| Sepal shape | |
| Overall | Elliptic |
| Apex | Typically acute |

TABLE 8-continued

| FLOWER CHARACTERISTICS | |
|---|---|
| Characteristic | 'TAMIR' |
| Base | Truncate |
| Sepal length (mm) | 10 mm to 12 mm |
| Sepal width (mm) | 4 mm to 6 mm |
| Sepal length/width ratio | Longer than broad |
| Number of sepals/flower | Typically 10, sometimes 20 |
| Corolla diameter (mm) | 30 mm to 34 mm |
| Calyx diameter (mm) | 35 mm to 40 mm |
| Size of calyx relative to corolla | Slightly longer |
| Size of inner calyx relative to outer calyx | Slightly smaller |
| Relative position of petals | Overlapping |

TABLE 9

| REPRODUCTIVE ORGANS | |
|---|---|
| Characteristic | 'TAMIR' |
| Androecium: | |
| Stamen: | |
| Number per flower: | About 20 to 30. |
| Filament: | |
| Length: | About 3 mm to 4 mm. |
| Color: | Light yellow green, closest to RHS 145D. |
| Anther: | |
| Length: | About 1 mm. |
| Color: | Yellow-orange, RHS 17A. |
| Gynoecium: | |
| Receptacles: | |
| Shape: | Spherical. |
| Length: | About 5 mm to 6 mm. |
| Diameter: | About 4 mm to 6 mm. |
| Color: | Green, RHS 143C. |
| Style: | |
| Length: | About 3 mm to 4 mm. |
| Color: | Dark yellow, closest to RHS 13A. |

TABLE 10

| PEST AND DISEASE REACTIONS | |
|---|---|
| Characteristic | 'TAMIR' |
| Two spotted spider mite | No testing/observations |
| Lygus bug | No testing/observations |
| Flower thrips | No testing/observations |
| Powdery mildew | Tolerant |
| Botrytis fruit rot | Moderately tolerant |
| Angular leaf spot | No testing/observations |

We claim:

1. A new and distinct strawberry plant named 'TAMIR', as herein described and illustrated by the characteristics set forth above, having a low number of daughter plants in the propagation nursery, not requiring chilling for flower induction, and having very early fruit production from the first week of November.

* * * * *